(12) United States Patent  
Mirza

(10) Patent No.: US 9,168,063 B2  
(45) Date of Patent: Oct. 27, 2015

(54) VOID CONTAINMENT APPARATUS AND METHOD OF USE FOR CREATING A SEALED ENVIRONMENT FOR PRODUCT DELIVERY

(76) Inventor: Faisal Mirza, San Francisco, CA (US)

( * ) Notice: Subject to any disclaimer, the term of this patent is extended or adjusted under 35 U.S.C. 154(b) by 1001 days.

(21) Appl. No.: 13/041,521

(22) Filed: Mar. 7, 2011

(65) Prior Publication Data

US 2011/0218544 A1 Sep. 8, 2011

Related U.S. Application Data

(60) Provisional application No. 61/311,348, filed on Mar. 7, 2010.

(51) Int. Cl.  
*A61B 17/58* (2006.01)

(52) U.S. Cl.  
CPC ...................................... *A61B 17/58* (2013.01)

(58) Field of Classification Search  
CPC .................. A61M 25/1011; A61M 25/1006; A61M 2025/1013; A61M 2025/1054; A61M 2025/1065; A61B 17/34; A61B 2017/3486; A61B 2017/3488; A61B 17/88; A61B 17/8855  
USPC ............ 600/204–207; 606/92–94; 604/95.03, 604/96.01, 99.01, 99.02, 99.03  
See application file for complete search history.

(56) References Cited

U.S. PATENT DOCUMENTS

| | | | | |
|---|---|---|---|---|
| 4,462,394 A | * | 7/1984 | Jacobs | 606/94 |
| 4,832,044 A | * | 5/1989 | Garg | 600/566 |
| 5,024,655 A | * | 6/1991 | Freeman et al. | 604/509 |
| 5,309,896 A | * | 5/1994 | Moll et al. | 600/207 |
| 5,361,752 A | * | 11/1994 | Moll et al. | 600/205 |
| 5,468,245 A | * | 11/1995 | Vargas, III | 606/94 |
| 6,358,266 B1 | * | 3/2002 | Bonutti | 606/190 |
| 7,758,644 B2 | * | 7/2010 | Trieu | 623/17.11 |
| 8,403,937 B2 | * | 3/2013 | Schwardt et al. | 606/92 |
| 2002/0068879 A1 | * | 6/2002 | Lubock et al. | 600/567 |
| 2007/0225219 A1 | * | 9/2007 | Boden et al. | 514/12 |
| 2008/0249604 A1 | * | 10/2008 | Donovan et al. | 623/1.15 |
| 2009/0299282 A1 | * | 12/2009 | Lau et al. | 604/99.01 |

FOREIGN PATENT DOCUMENTS

WO WO02096308 12/2002

* cited by examiner

*Primary Examiner* — Anu Ramana  
(74) *Attorney, Agent, or Firm* — Nabeela Rasheed

(57) ABSTRACT

A void containment apparatus and its method of use during an invasive procedure on the body are disclosed. The void containment apparatus includes an elongated housing and a balloon. The balloon is capable of being inflated and deflated. When inflated, the balloon provides a seal around a void and allows delivery or extraction of material into or out of the void with minimal leakage outside the void.

16 Claims, 9 Drawing Sheets

VOID CONTAINMENT APPARATUS AND METHOD OF USE FOR CREATING A SEALED ENVIRONMENT FOR PRODUCT DELIVERY

CROSS-REFERENCE TO RELATED APPLICATIONS

This application claims the benefit of the filing date of: U.S. Provisional Patent Application No. 61/311,348, which was filed on Mar. 7, 2010, is entitled VOID CONTAINMENT APPARATUS AND METHOD OF USE FOR CREATING A SEALED ENVIRONMENT FOR PRODUCT DELIVERY. The contents of U.S. Application No. 61/311,348 are hereby incorporated by reference as part of this application.

TECHNICAL FIELD

The present invention relates generally to an apparatus used during surgery or an invasive procedure to the body. More specifically, the present invention relates to an apparatus used in an arthroscopic or laparoscopic environment to provide a sealed environment to permit product flow (e.g., fluid, paste, or a semi-solid material) to and from a void.

BACKGROUND OF THE INVENTION

Bones, whether human or animal, can develop defects (e.g., a void or cavity in the bone) that can compromise their structure. These defects can occur due to various reasons, such as osteopenia, degeneration, prior surgery, fractures, bone cysts, or trauma. Additionally, after prior surgery for ligament reconstruction of the knee, a residual implant or graft passage tunnel creates a defect. If the implant or graft fails, revision surgery may first require filling of this defect prior to subsequent implantation.

In another example, in the shoulder, such as rotator cuff surgery, prior suture anchors that pull out or fail can leave a bone void that needs to be filled, otherwise revision surgery is not possible with anchor placement in that location. With disuse osteopenia, cystic degeneration can cause the bone structure to be compromised. In other cases, traumatic injury can create defects in the bone. In osteoporosis, bone quality can be reduced such that primary implant insertion fails due to weakened structure and may require some form of supplementation (such as filling of the defect with a cement like substance) to allow surgery to be completed. These defects in the bone can limit the capacity for various implants or grafts to be secured within the bone. As such, this can lead to situations where the bone may need to be grafted or augmented prior to securing the implant or graft, either immediately or in a staged manner with multiple surgeries.

Regardless of how the defect occurred, various solutions have been explored to fix the defect, but they all lack in one way or another. One problem with the existing method is it does not allow containment of the cement like substance within the bone defect. Often, the material spills over and around the bone defect and causes intrusion into and around the joint and surrounding tissues. Since the cement like substance tends to harden over time, it creates a solid structure into other areas of the body thereby causing crystalline deposits inside the joints. These deposits can be harmful to the body causing several types of medical issues, such as cartilage degeneration, tissue foreign body reaction and pain.

Bone defects vary in shape and size and the defect often contains uneven surfaces. The current methods do not provide a mechanism to contain the cement like substance inside the uneven shaped defect and result in allowing the cement like substance to leak and escape to other parts of the body. The escaped substance causes visualization issues for the surgeon and several medical problems as explained earlier.

Yet another problem with existing solutions is visualization. The current procedures for reconstituting the void in the bone, thereby fixing the defect, require a surgeon to create a working portal and visualizing portal. The working portal is established through an incision made at or around the area requiring surgery (the operative field) and allows the surgeon to perform surgery on the defect using surgical tools through a subsequent portal. The visualizing portal provides visual access to the operative field such that the surgeon can see the area of surgery while performing the surgery. Visualization is critical and key to a good and successful outcome with surgery. Existing methods are unable to deliver the cement like substance to fix bone defects without blocking surgeon's line of sight to the operative field. Since the current methods cannot contain the cement like substance within the defected bone cavity, the excess material either protrudes out of the defected cavity or accidentally gets deposited outside the cavity blocking the surgeon's vision during the procedure.

Bone defects can have various depths, contours, and ruggedness. Although Current methods allow depositing of the cement like substance into the defect, they cannot achieve a thorough penetration of the cement like substance into the interstices of the bone structure. This is largely because pressure needs to be applied in order to achieve a thorough penetration of the cement like substance into the interstices of the bone structure. Since current methods (in arthroscopy) cannot contain the cement like substance within the defected cavity, applying pressure only increases the problem by allowing even more substance to escape from the defect and into other regions of the body.

Thus there is a need for a solution to address the concerns mentioned above.

SUMMARY OF THE INVENTION

In one embodiment of the invention, an apparatus having an adjustable balloon is used. The balloon is capable of being inflated (or deflated) through various means and adjusted to a desired size. The balloon allows a seal to be created around the surgical area, such as a void, and prevents any filler material, such as the cement like substance, from escaping.

[0010] In another embodiment of the invention, the apparatus includes multiple balloons. A first balloon is placed near the distal end of the apparatus, which has an opening for depositing a substance in a defect (or void). A second balloon near the proximal end of the apparatus that prevents any tissue from entering the surgical space. Both balloons are capable of being inflated (or deflated), adjusted to a desired size, and used for creating a seal around their environment.

In another embodiment of the invention, the apparatus includes an adjustable balloon and multiple chambers. An inner chamber for depositing and delivering a filler material that needs to be delivered to the human or animal body, such as cement like substance for filling bone defects, and an outer chamber that encapsulates the inner chamber. Both outer and inner chamber have an opening that is exposed towards the void. In operation, the outer chamber and the inflated balloon create an outside seal surrounding the void. The outer chamber includes ports that allow entry and exit of fluid or any medium through the outer chamber. As such fluid or gas can pass through from one end of the outer chamber (e.g., proximal end) to the other end of the outer chamber (e.g., distal end) and flow through its distal port into and around the void, which is sealed by the distal balloons 222, to remove any excess deposit material that remains after filling the void, or allow escaping air from pressurization.

In another embodiment, only the inner chamber is exposed to the void with the outer chamber isolated from the void. In this situation, the outer chamber may remain empty while delivery of filler material is being performed using the inner chamber. Alternatively the outer chamber may be filled with gas or fluid while the inner chamber is being used. Among many benefits, one reason for this configuration is to regulate the temperature of the inner chamber through the temperature controlled gas or fluid in the outer chamber.

In another embodiment of the invention, the apparatus can be used as an endoscopic, laparoscopic, or arthroscopic device. For example, in an endoscopic embodiment, if a void is created, the balloon can create a seal surrounding the void and prevent leakage of fluid to areas surrounding the void and create a separation of environment between the void and its surroundings. For example, for arterial lines, a catheter is placed into the vessel to allow delivery of wires or stents or measurements of pressure. The entry site, however, is secured by hand, tape, or suture on the skin to prevent movement of the catheter. With balloon inflation anywhere along the catheter tip within and/or outside the lumen of the vessel, the catheter can be secured directly to the vessel wall or lumen. Likewise, in a laparoscopic environment, the device can be used for delivery of a gel like substance to an organ or body defect where the sealing or separation of the environment is needed.

In yet another embodiment, the void containment apparatus may be used in environments outside of the arthroscopic or laparoscopic environment. For example, a defect in the shoulder may be fixed through a larger incision, open approach, whereby the skin and tissues are moved away from the defect or operative field providing direct access from outside a body to the defect. Since no small incision is needed, an attempt to fix the defect can be made without using arthroscopic procedures. The void containment apparatus may also be used in these situations to seal the defect by delivering any product into the defect.

Advantages of the Invention

One advantage of the present invention is that it provides a sealed environment for delivering a product, such as a filler material, to a void or defect.

Another advantage of the present invention is that is allows the creation of a seal surrounding a void and separates the sealed region from its surroundings, such as the remainder of the joint in a knee or shoulder arthroscopy.

Yet another advantage of the present invention is that it allows pressurization of a filler material into the void.

Another advantage of the present invention is that it prevents leakage of the filler material to the surrounding of a void, which results in preventing joint or body cavity damage.

Yet another advantage of the present invention is that it allows a medical professional, such as an orthopedic surgeon performing a surgery, to maintain visualization during surgery and delivery and solidification of the filler material.

Another advantage of the present invention is that it allows immediate, one stage securing of graft or implant without a second operation needed to allow time for the autograft or allograft to heal the defect after the first operation.

Yet another advantage of the present invention is that in an arthroscopic environment it allows a second or proximal balloon to create a seal in the area of incision and improves visualization, prevents fluid from leaking outside the body, and prevents encroaching of tissues inside the body.

BRIEF DESCRIPTION OF THE DRAWINGS

The foregoing summary, as well as the following detailed description, will be better understood when read in conjunction with the appended drawings. For the purpose of illustrating the invention, there are shown in the drawings examples that are presently preferred. It should be understood, however, that the invention is not limited to the precise arrangements and instrumentalities shown. In the drawings.

DETAILED DESCRIPTION

The subject invention will be described with reference to numerous details set forth below, and the accompanying drawings will illustrate the invention. The following description and drawings are illustrative of the invention and are not to be construed as limiting the invention. Numerous specific details are described to provide a thorough understanding of the present invention. However, in certain instances, well known or conventional details are not described in order to not unnecessarily obscure the present invention in detail.

It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this invention belongs.

Figure 1A:
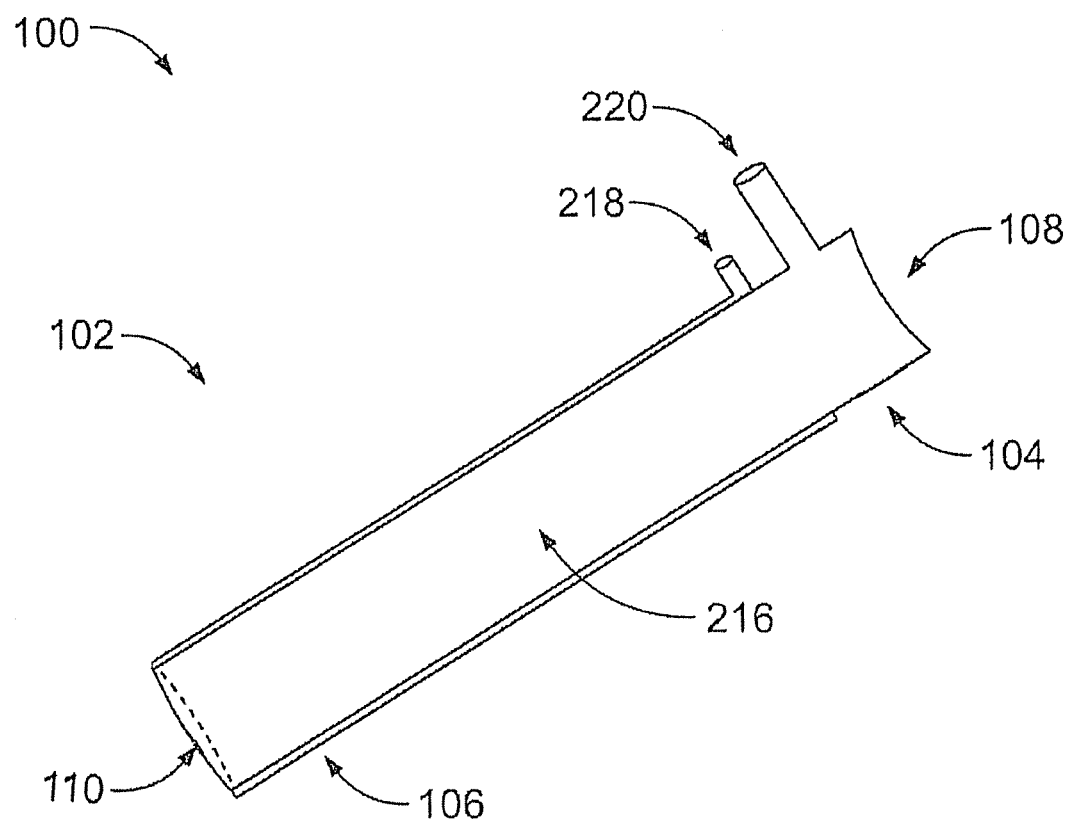
FIG. 1A illustrates one embodiment of the Void containment apparatus with the distal balloon in its deflated stage.

FIG. 1A illustrates one embodiment of the void containment apparatus 100 in its deflated stage. The void containment apparatus 100 includes a housing 102. The housing 102 is not limited by its shape or material. For example, materials such as plastic, metal, wood, composite, or any biologically inert material may be used for the housing 102. Further, housing shapes may include cylindrical, rectangular, or conical shapes that may be symmetrical or asymmetrical. The housing 102 is not limited in size or dimension in any axis or plane. The housing 102 is also not limited to any texture. It can be rugged, plain, smooth, or have any variety of contours. It may also be translucent, transparent, opaque, or any variation in-between.

The housing 102 includes an elongated hollow chamber 216 that has a proximal end 104 and a distal end 106. Both the proximal and distal ends have an opening to the outside of the void containment apparatus 100. The opening 108 at the proximal end 104, which may also be described as an entry portal 108, and the opening 110 at the distal end 106, which may also be described as an exit portal 110, may be of different size, shape and dimension. Additionally, the entry portal 108 and the exit portal 110 may be similar or distinct from each other in size, shape or dimension.

Figure 1B:
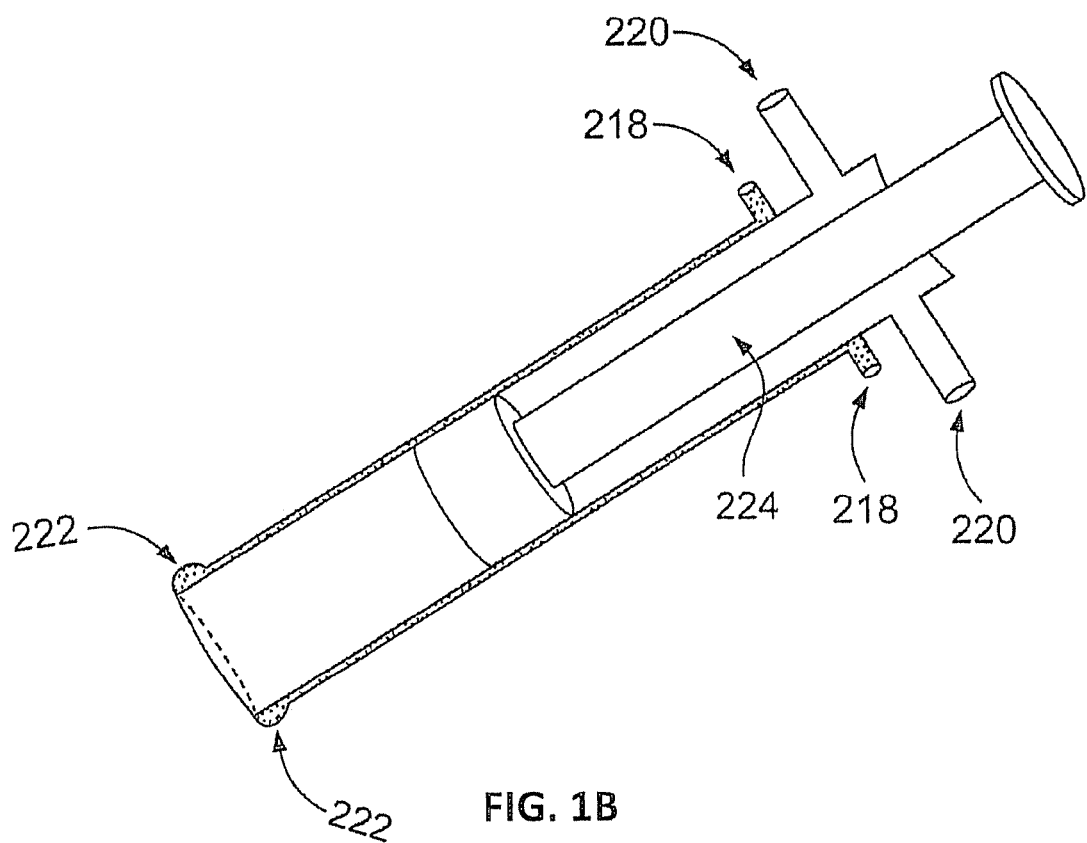
FIG. 1B illustrates one embodiment of the void containment apparatus with the distal balloon in its inflated stage.
Figure 1C:
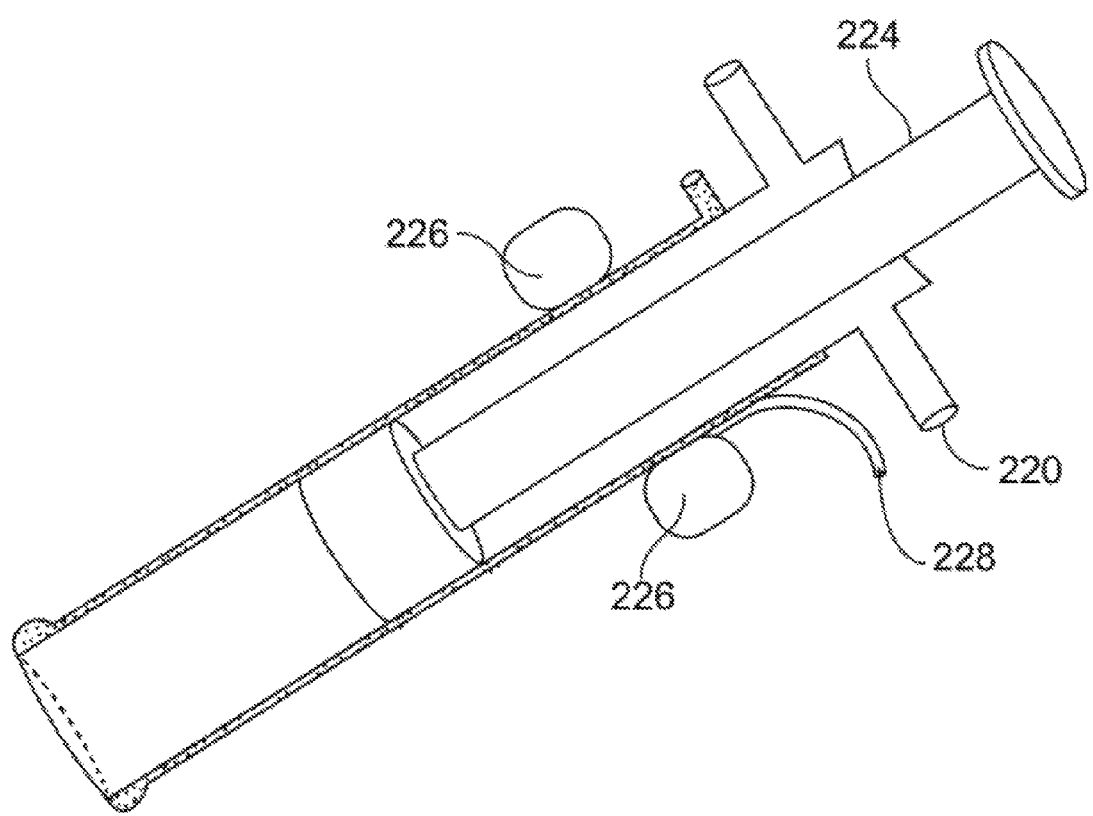
FIG. 1C illustrates one embodiment of the void containment apparatus with a distal and proximal balloons in their inflated stages.

The entry portal 108 allows the insertion of any insertion device 224, such as a piston, syringe, trocar, or any surgical instrument or material, into the chamber 216. For example, FIG. 1B illustrates a plunger as an exemplary insertion device 224 and FIG. 1C illustrates a trocar as an exemplary insertion device 224.

The entry portal 108 may be a hole or opening through the housing 102 from its distal end 106 that allows the entry of the insertion device 224 mentioned above. In another embodiment, the entry portal 108 may include any form of deformable or penetrable seal of any composition, material, texture, or elastomeric composition. In such an embodiment, an insertion device 224 may be inserted into the chamber 216 through the entry portal 108 after the insertion device 224 has penetrated through the deformable or penetrable seal.

Upon insertion through the entry portal 108, the insertion device 224 may form a seal around the entry portal 108. The seal may prevent complete or partial entry of air, liquid, or material from entering or escaping from the chamber 216 though the entry portal 108. Alternatively, the entry portal 108 may include a supplementary housing or sealing material that maintains or creates a complete or partial seal upon the insertion of the insertion device 224.

The chamber 216 of the housing 102 is a hollow cavity that allows insertion of any insertion device 224 or material. The chamber 216 can be of any size, shape, or dimension. The chamber 216 may allow any insertion device 224 that is inserted through the entry portal 108 (i.e. near the proximal end 104) to travel through the elongated chamber 216 from its proximal 104 to its distal end 106. The chamber 216 may also have stops preventing or limiting the travel of the insertion device 224 to a desired length.

The chamber 216 may be used to house or transport any filler material 230. Filler material 230 may be any injectable type substance, cement like substance (e.g., β-tricalcium phosphate), plasma type material, glue like material, gel like material, a material that changes form from a more liquid to a less liquid stage, such as from a flowing to a more stabilized phase, a material that does not change its state, or any other material that solidifies, hardens, firms, cures, or agglutinates once deposited.

At the distal end of the chamber 216, the exit portal 110 provides an exit for the insertion device 224, either entirely or a portion of the insertion device 224 such as a needle, or material. In one embodiment, a material may be deposited into the chamber 216 and then pushed there through by the insertion device 224 to exit from the distal end 106 of the chamber 216. The exit portal 110 may also include a seal or a mechanism that prevents the unwanted exit of the insertion device 224 or the material from the chamber 216. In another embodiment, the chamber 216 could be filled with filler material 230 through the exit portal 110 through any manner prior to insertion into the body.

The distal end of the housing 102 includes a distal balloon 222. The distal balloon 222 may cover the entire outer periphery of the housing 102 on its distal end 106 thereby circulating around or encapsulating the exit portal 110 without covering the opening of the exit portal 110. Alternatively, the balloon 222 may surround a partial section of the exit portal 110 while leaving the opening of the exit portal 110 uncovered. The distal balloon 222 may be permanently fixed or detachable either partially or completely from the housing 102. The distal balloon 222 may vary in size, shape, and dimension and/or be fully adjustable. The distal balloon 222 may be made of any material that allows it to expand and contract to a desired shape and size. Any material, gas, or liquid may be used to inflate or deflate the balloon.

The distal balloon 222 may be inflated or deflated to its fullest or partial capacity. The void containment apparatus 100 may include mechanisms that allow its user to inflate or deflate the balloon 222 to its desired shape and size at any desired inflation or deflation rate. Once inflated to its desired shape and size, the distal balloon 222 creates a seal surrounding a void 30 and isolating the void 30 from its surroundings. This seal prevents escaping of the filler material 230 that is deposited by the void containment apparatus 100 into the void 30. The seal is a temporary enclosure created by the balloon 222 during the use of the void containment apparatus 100, i.e., once the void containment apparatus 100 is extracted away from the void 30, or if the balloon 222 is deflated, the seal is removed.

In one embodiment, the mechanism for inflating or deflating the balloon 222 may be through a distal balloon port 218 and/or conduit that is coupled to the housing 102 in any manner. The distal port 218 and conduit may be of any shape, size, or material. An inflation source, such as a gas or liquid providing source, may be coupled with the distal balloon port 218 to inflate or deflate the balloon 222. The distal balloon port 218 may be located anywhere along the housing 102 and may be rigid or flexible.

In another embodiment, the mechanism to inflate or deflate may be integrated or made part of the housing structure 102. In yet another embodiment, the inflating and deflating mechanism may be located outside the void containment apparatus 100.

As shown in FIG. 1C, the void containment apparatus 100 may include one or more balloons 226 in addition to the distal balloon 222. The additional balloons 226 may be located anywhere on the housing 102. The void containment apparatus 100 may also allow the movement, adjustment, and locking of the additional balloon 226 along its elongated housing 102 thereby allowing its user to position the additional balloons 226 closer or farther from the distal or proximal ends 106, 104 of the housing 102. For example, void containment apparatus 100 may include a proximal balloon 226 that may be permanently fixed or detachable either partially or completely from the housing 102 and located closer to the housing's proximal end. The proximal balloon 226 may vary in size, shape, and dimension and/or be fully adjustable. The proximal balloon 226 may be made of any material that allows it to expand and contract to a desired shape and size.

The proximal balloon 226 may include a separate port 228 which may be used for filling the proximal balloon 226 with any material, gas, or liquid to inflate or deflate the balloon 226. The proximal balloon port 228 may be attached or detached from the housing 102 and may be rigid or flexible. Alternatively, a single port connected with conduits to each balloon 222, 226 may be used to inflate or deflate any balloon of the void containment apparatus 100. The proximal balloon 226 may be similar or distinct from the distal balloon 222.

In one embodiment, the proximal balloon's 226 function may be used to create an outer seal during a surgical procedure. For example, in a surgical setting, a medical professional, such as an orthopedic surgeon, may create two incisions into a patient when trying to fix a void 30 in the patient's bone. A first incision may be created for inserting a visualization device, such as an arthroscope or laparoscope, and a second incision for inserting the void containment apparatus 100 into the patient's body. The first incision allows the medical professional to visualize the void 30 and the surgery being performed on the void 30. In this scenario, if the void containment apparatus 100 is inserted through a patient's tissues and into a void 30, the distal balloon 222 forms a seal around the void 30 and the void containment apparatus 100 (as mentioned above) while the proximal balloon 226 may form a seal around the tissues and the void containment apparatus 100. The seal formed by the proximal balloon 226 prevents the tissue from intruding towards the void 30 and into the surgeon's field of vision.

The housing 102 may include one or more supplemental ports 220 that may vary in shape and size. The supplemental ports 220 may be placed at any location on the housing 102. The function of the supplemental port 220 may be to allow any material into and out of the chamber 216. In one embodiment a first supplemental port 220 may be used to deposit filler material 230 into the chamber 216 and a second supplemental port 220 for allowing a non-filler material into the chamber 216. Alternatively a single supplemental port 220 may be used for allowing the entry and exit of any material into and out of the chamber 216.

The various features and embodiments of void containment apparatus 100 as described in FIGS. 1A, 1B, and 1C are interchangeable and may be used in any combination. Further, in addition to the embodiments and combinations described above, the void containment apparatus can be any housing with a balloon that allows creation of a seal around the void. Additionally, the void containment apparatus may include additional attachment or features that assist or enhance the delivery of the filler material into a void. Such attachment or features are also contemplated. For example, the void containment apparatus may include an automated mechanism that allows determination of the amount of filler material needed for any void and allow precise amount of filler material to inserted into the void, such as by the insertion device stopping at a particular stage to ensure only a precise amount of filler material, no more or no less is deposited into a void.

Figure 2A:
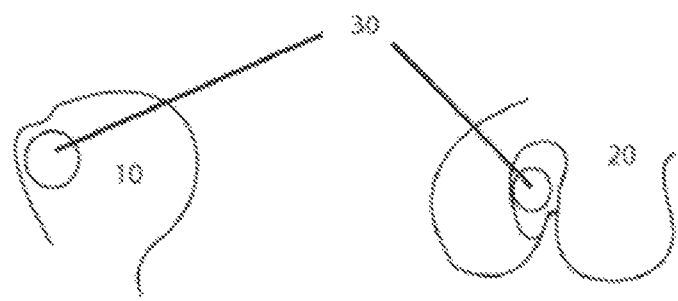
FIG. 2A illustrates an exemplary void in the humerus or the knee.

FIG. 2A illustrates an exemplary void 30 in the humerus 10 or the knee 20. The void 30 may be a defect within bone or tissue that can potentially compromise structural integrity or ability to secure any type of implant or graft (e.g., artificial, natural, autogenic, allogenic, biologic or non-biologic implants). The void 30 may also be any tunnel, passage or hole, created or encountered naturally or mechanically, contained or uncontained. Further, the void 30 may exist in any human or animal and may be found in tissue, any body cavity, or organ. The exemplary void 30 illustrated in FIG. 2 of the humerus 10 is in the proximal humerus 10 and in the region of the greater tuberosity. The exemplary void 30 in the knee 20 is shown on the medial aspect of the lateral femoral condyle.

Figure 2B:
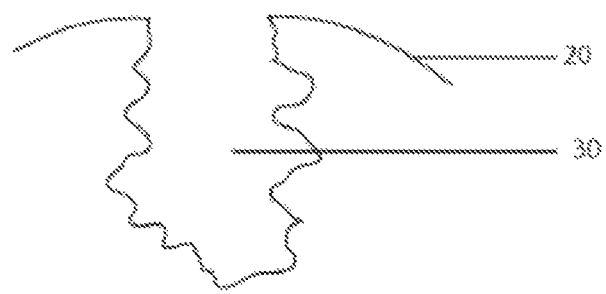
FIG. 2B illustrates is a detail sectional view of an exemplary void in a knee.

FIG. 2B illustrates is a detail view of an exemplary void 30 in a knee 20. As illustrated, the void 30 can have different shapes, sizes, depth, ruggedness, contours, and surface regions.

Figure 3:
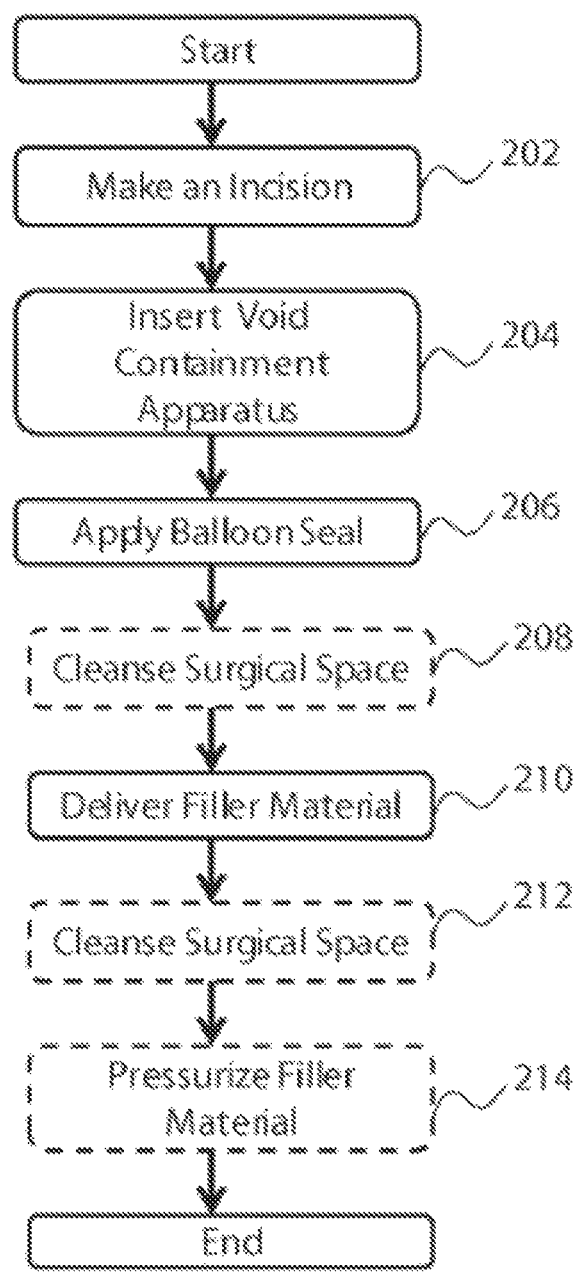
FIG. 3 illustrates one exemplary flow chart of how the void containment apparatus may be used in an arthroscopic environment.

FIG. 3 illustrates one exemplary use of the void containment apparatus 100 in an arthroscopic environment. More specifically, FIG. 3 illustrates exemplary steps that may be performed by a medical professional, such as an orthopedic surgeon, in performing surgery to fix a void 30 in a patient's bone by filling it up with filler material 230. Any of the void containment apparatuses as described and shown in FIG. 1A, 1B or 1C may be used.

At 202, multiple incisions are made in the patient's body in order to perform the surgery. One incision (void incision) is made in the proximity of the void 30. An exemplary void 30 can be seen in FIGS. 2A and 2B. This void incision penetrates through the patient's skin and tissue and provides an opening to the void 30. Various well known techniques are used to perform the incision. This incision allows any instrument or an apparatus, such as the void containment apparatus 100, to be inserted through the patient's skin and tissue and into or near the void 30.

Another incision (visualization incision) is made away from the void 30. This incision provides visualization of the void 30 and the space around the void 30. The purpose of this incision is for the medical professional performing the surgery to be able to visualize the void 30 and the surgical instruments or apparatuses being used in or around the void 30 such that surgery can be performed with precision and accuracy. A visualizing instrument, such as an arthroscope, can also be inserted though the visualization incision for providing a visual of the void 30 and the surgery that is being performed on it. In a non arthroscopic setting, the amount and type of incisions, or the procedure for making the incision may vary.

Figure 4A:
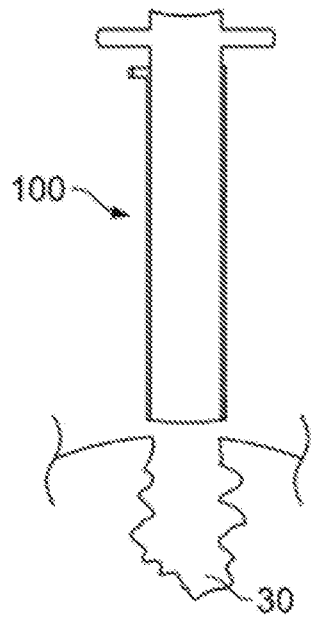
FIG. 4A illustrates an exemplary operation of the void containment apparatus where the void containment apparatus is approaching the area of the void.

At 204, the void containment apparatus 100 is inserted through the incision and into or towards the void 30. FIG. 4A illustrates one embodiment—here the void containment apparatus 100 is being inserted through or towards a patient's void 30 (after already having been inserted through the patient's tissue). Optionally, a trocar can be used to facilitate the insertion of the void containment apparatus 100. When used, the trocar provides structural support and alignment for the void containment apparatus 100.

The insertion of the void containment apparatus 100 through the void incision (or working portal) and into or towards the void 30 can be visualized by the medical professional by using the visualization incision. The medical professional can align and maneuver the void containment apparatus 100 to their desire, visualize the alignment through the visualization incision, and accurately insert the void containment apparatus 100 onto the surface of the void 30 or into the void 30. One could measure the size of the void 30 diameter to determine the correct diameter of void containment apparatus 100 needed.

At 206, a balloon 222, which is a part of the void containment apparatus 100, may be inflated. Once the medical professional has entered the void 30 or brought the void containment apparatus 100 in close proximity to the void 30, the medical professional can cause the balloon 222 to be inflated.

Any of the inflation mechanisms described above may be used. Once inflated, the balloon 222 creates a seal around the void 30.

Figure 4B:
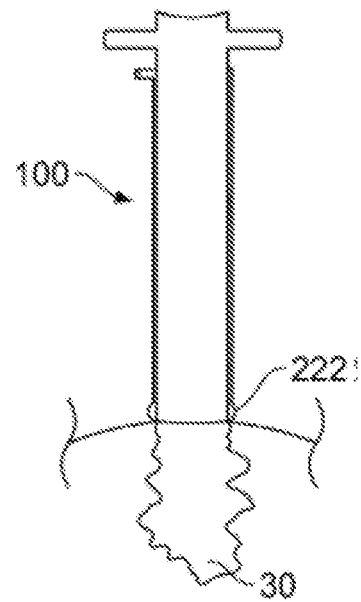
FIG. 4B illustrates the an exemplary operation of the void containment apparatus where the balloon is being inflated to seal the area surrounding the void.

One embodiment of the inflated balloon 222 and the seal created is shown in FIG. 4B. Here, the distal balloon 222 is being inflated to seal the area surrounding the void 30. Once the apparatus is seated upon the void 30, or inserted into the void 30, the balloon 222 is used to create a seal.

At 208, the medical professional can perform an optional step of cleansing the void 30, the area around the void 30, or the chamber 216 and distal port 218 of the void containment apparatus 100. Cleansing may be performed by flushing through a fluid to remove any debris, blood, bone chips, or matter that is in or around the void 30, chamber 216, or the distal port 218 of the void containment apparatus 100. A cleansing (irrigation, arthroscopic) fluid or gas may be provided through any of the inlet ports of the void containment apparatus 100, such as the supplemental port 220. Since the balloon 222 provides a seal around the void 30, the cleansing fluid may be used without substantial leakage outside the sealed environment.

At 210, filler material 230 may be delivered into the void 30 using the void containment apparatus 100. The filler material 230, as described above, is in a flowing or viscous state, and is placed in the chamber 216 of the void containment apparatus 100. The medical professional may deposit the filler material 230 by various means into the void 30. One method of deposition may be by pressing an insertion device 224, such as a piston, syringe plunger, trocar, or similar surgical instrument, through the chamber 216 in the direction of the void 30 and having the filler material 230 deposited upon pressure being applied to the insertion device 224. Alternatively, the void containment apparatus 100 may provide some automatic means for pushing though the material through the chamber 216 and into the void 30.

Figure 4C:
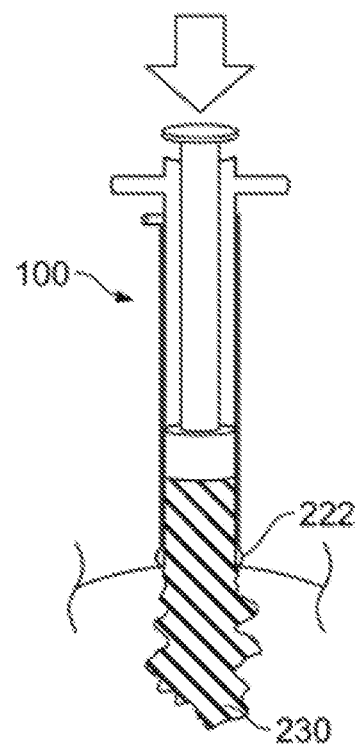
FIG. 4C illustrates an exemplary operation of the void containment apparatus where the filler material is delivered into the void.

The filler material 230 may be deposited until the entire void 30 is filled with the filler material 230. FIG. 4C illustrates an exemplary operation of the void containment apparatus 100 where the filler material 230 is delivered into the void 30. One important aspect of the invention is that the balloon 222 provides a seal around the void 30 such that the filler material 230 does not escape outside the sealed environment, or at a minimum permits only a minor amount of leakage outside the sealed environment.

At 212, similar to step 208, the medical professional may optionally choose to cleanse around the void 30 after the filler material 230 has been deposited. The cleansing removes any excess filler material 230 or other material from the surgical site. Since the filler material 230 takes time to harden or cure inside the void 30, the medical professional may choose to cleanse after the curing has taken place to such a degree that the cleansing will not remove any filler material 230 from inside the void 30. The cleansing may be performed by replacing the cleansing fluid into the chamber 216 and flushing around the surgical site. Alternatively, cleansing may occur prior to curing or hardening of the filler material 230, if needed, by removing the insertion device 224 and removing excess filler material 230. The cleaning process may also occur at any intermediate stage between depositing and hardening or curing of the filler material 230.

At 214, the medical professional may optionally choose to pressurize the deposited filler material 230. Pressurization may include applying a desired amount of pressure using the distal end of the void containment apparatus 100 on the filler material 230 deposited in the void 30. As will be explained below, pressurization will force the filler material 230 thoroughly into the void 30 and allow it to penetrate into the interstices of the bone structure and create a strong bond due to interdigitation of the product with the bone. Since the void containment apparatus 100, using the balloon 222, provides a sealed environment, pressurization can be achieved without having the filler material 230 spill and leak extensively outside the void 30 and into the neighboring areas. Optionally, similar to steps 208 and 212, the medical professional may choose to cleanse around the void 30 after pressurization.

Although not displayed in FIG. 3, the medical professional may also install an implant, such as a screw or anchor, into the void 30 and deposit filler material 230 around the void 30 thereby securing the implant in place as the filler material 230 hardens. FIG. 6 further illustrates the concept of installing implants. Other uses of the void containment apparatus 100, such as in a laparoscopic environment, for example to deliver or extract fluid or substance in and out of an organ or tissue or vessel are also contemplated.

Figure 5A:
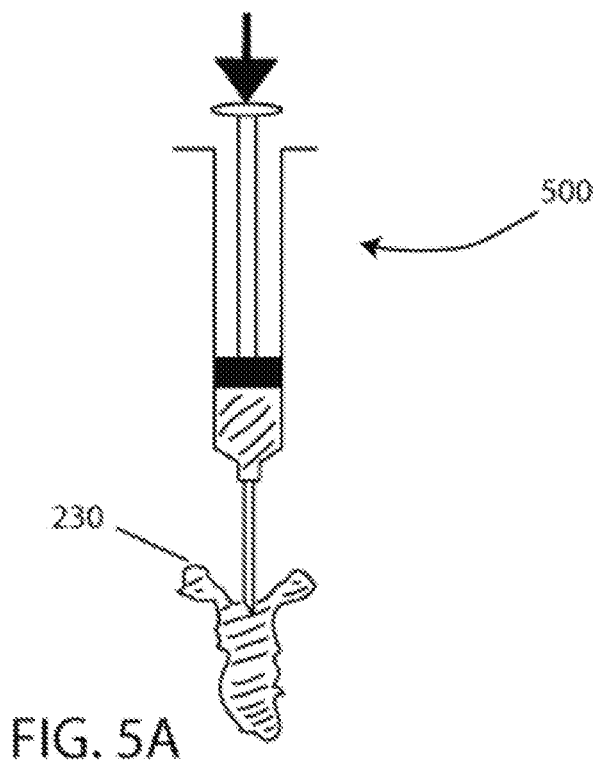
FIG. 5A illustrates a leak problem that exists in current systems.

FIG. 5A illustrates a leak problem that exists in current methods for delivery of the filler material 230. As shown, a syringe 500 is used for depositing filler material 230 into a void 30. Under the current methods, the filler material 230 cannot be contained and is likely to spill around the void 30. The current methods also do not allow proper filling of the void 30 without having it over or under filled. The filler material 230 also cannot be pressurized since application of any pressure in a non enclosed environment will cause the filler material 230$s$ to overflow from the void 30 and into other parts of a patient's body. As described in the background, the spill or overflow causes medical problems for the patient and visualization problems for the medical professional.

Figure 5B:
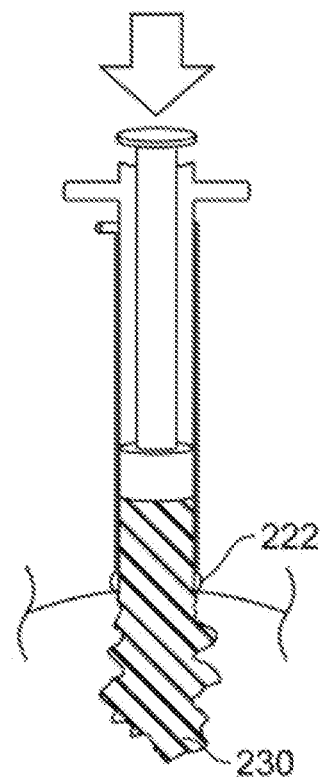
FIG. 5B illustrates an exemplary operation of the void containment apparatus where pressurization is used to achieve interdigitation.

FIG. 5B illustrates an exemplary operation of the void containment apparatus 100 where pressurization is used to achieve interdigitation. Since the void containment apparatus 100 uses a balloon 222 to create a seal around the void 30, it prevents spill or excessive leakage of the filler material 230. The sealed environment allows application of pressure onto the filler material 230 such that the filler material 230 enters the interstices of the bone structure and creates a strong bond due to interdigitation of the filler material 230 and the bone. As such, as the filler material 230 hardens or cures within the void 30, it fills void 30 without leaving large gaps. Additionally, since the sealed environment allows pressurization (and if required, removal of filler material 230 through cleansing), an appropriate and desired amount of filler material 230 can be deposited without the void 30 being over or under filled.

Figure 6A:
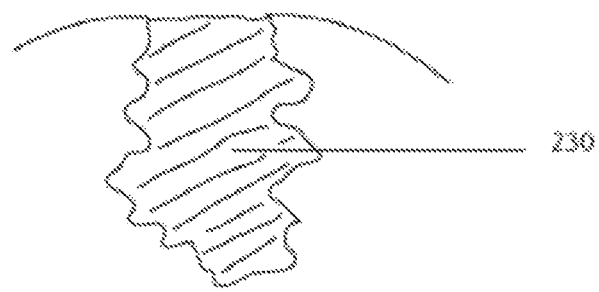
FIG. 6A illustrates an example of a void filled with material (after delivery and removal of void containment apparatus)
Figure 6B:
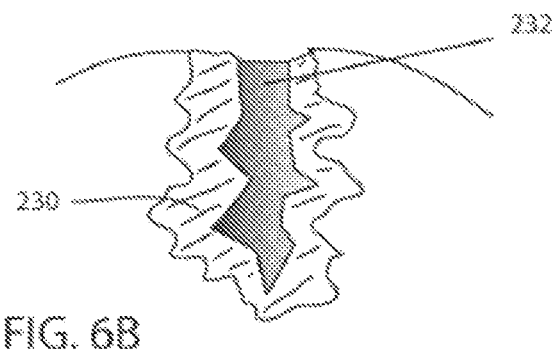
FIG. 6B illustrates an example of a void filled with material (after delivery and removal of void containment apparatus) and an implant seated within the void; and [0036]
Figure 6C:
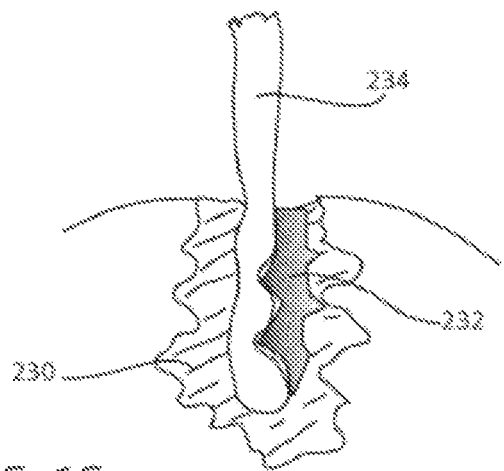
FIG. 6C illustrates another illustration of an implant seated in the void and filler material surrounding the implant.
Figure 7:
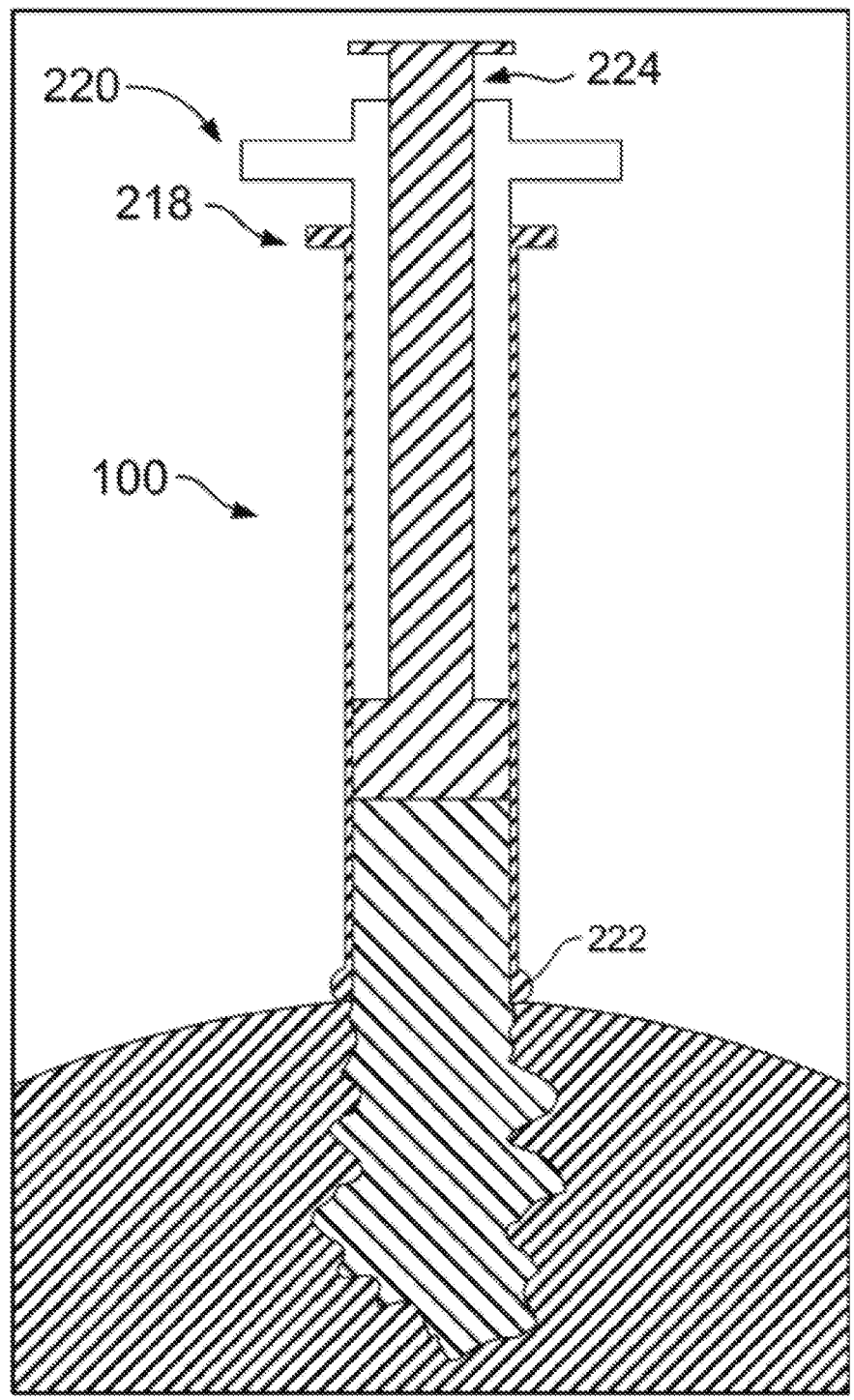
FIG. 7 an illustrates an example of a void filled with material using apparatus 100 showing multiple ports 220 on the inner chamber, and multiple ports 218 on the outer chamber, which multiple balloons 222 outside of the void forming a seal in an inflated configuration.

FIGS. 6A, 6B, and 6C illustrate various examples of voids 30 and implants that may be deposited within the voids 30. FIG. 6A illustrates an exemplary void 30 after delivery of the filler material 230 and removal of void containment apparatus 100. Once the filler material 230 hardens or cures, the void 30 is filled and a strong bond is created between the filler material 230 and the void 30. After completion and curing, the void's 30 irregular shape and its outer surface is restored back to its original shape, or a close approximate, i.e., the void containment apparatus 100 allows for exact, or a close, matching of the void 30 contours for a proper restoration.

FIG. 6B illustrates an example of a void 30 having an implant 232 and filler material 230 230 surrounding the implant 232. Here, a medical professional may install and place an implant 232 in its desired location within the patient's bone. Once the implant 232 is placed and positioned, filler material 230 may be poured around the implant 232. As the filler material 230 hardens or cures, it provides structural integrity to the implant 232 and holds it in the desired location. Alternatively, other methods, such a pouring filler material 230 to a desired level, such as to fill only a part of the void 30, and then depositing and installing the implant 232 are also contemplated.

FIG. 6C illustrates another illustration of an implant 232 seated in the void 30 and the filler material 230. In this illustration, a tissue 234 (bone and/or tendon for example) is embedded within the filler material 230. This may be achieved by inserting the implants 232, 234 into the filler material 230 until cured; or inserting them into a reamed tunnel after the filler material 230 cures satisfactorily.

Both in FIGS. 6B and 6C, in one instance, the implant 232 is inserted after the filler material 230 hardens. With the void 30 reconstituted with hardened filler material 230, this allows preparation of a tunnel or passage for graft or implant 232 insertion and securing. The new preparation of tunnel may not be limited to the region of the void 30 alone but in fact may even involve and overlap unadulterated bone or tissue as part of the tunnel or passage.

Implants 232, as discussed in FIGS. 6B and 6C, can be situated or placed in the void 30 to any depth or degree, e.g., partially inserted, interested half way, or whole inserted to the full depth of the void 30. The implant 232 may be placed in the void 30 at any stage of filler material 230 being deposited into the void 30. For example, the implant 232 may be placed when the void 30 is filled with filler material 230, before delivery of the filler material 230 into the void 30, after delivery of the filler material 230 into the void 30 but before curing, during delivery of the filler material 230 into the void 30, or after delivery and curing in any manner.

In another instance an implant 232 may be placed into the void 30 after the filler material 230 has been delivered into the void 30 and cured. This can be accomplished by reaming a tunnel of desired depth into the bone and void 30 and prepared to receive an implant 232 that can be secured in any manner, such as press-fit or screw.

The structure and use of the void containment apparatus 100 is not limited to the embodiments described above. For example, in an endoscopic environment, a catheter, such as an arterial line can be inserted with proximal and distal balloons 226, 222 inflated to maintain seal and security of catheter during measurements. In laparoscopic environment, a tissue or organ defect can be filled with a haemostatic agent, such as fibrin, and delivered to a specific void 30, and maintained there with the void containment apparatus 100. Other endoscopic and laparoscopic uses and procedures using the void containment apparatus 100 are also contemplated.

In yet another embodiment, the void containment apparatus 100 may be used to deliver solid matter into a void 30. For example, allograft or autograft bone delivery to a void 30. A medical professional desiring to pack and fill a void 30 with bone chips can use the void 30 containment apparatus 100 to create a seal around the void 30, deliver the bone chips into the void 30, and impact or pack the bone chips into the void 30. Further, the void containment apparatus 100 may be used to deliver any combination of solid matter with the filler material 230 or allow its user to deposit filler material 230 before, during, or after the deposition of the solid matter. In a similar embodiment, the solid matter could be any type of fixation implant or device, such as an intramedullary nail, or any other hardware made of any combination of material(s); metal, non-metal, absorbable, non-absorbable, among others.

In another embodiment, the void containment apparatus 100 may be used to isolate a neoplasm, such as in a cancerous environment, during biopsy or treatment. Since neoplastic tumor cells can contaminate surrounding non-neoplastic tissue, it is critical during biopsy to remove the neoplastic cells in such a manner that they are not spilled into the surrounding areas. Typically, the procedure to remove these neoplastic cells involves creation of a void 30 in the region of the neoplasm. The void containment apparatus 100 (through its balloon 222) can be used in such a procedure to provide a seal surrounding the point of extraction of the neoplastic cells and its surroundings such that they can be removed without contamination. Additional uses besides extraction, such as reconstitution of the void 30 are also contemplated.

In the foregoing specification, the invention has been described with reference to specific exemplary embodiments thereof. It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention as defined by the appended claims. The specification and drawings are, accordingly, to be regarded in an illustrative sense rather than a restrictive sense.

The invention claimed is:

1. An apparatus for providing a seal around a void, wherein a void is cavity or defect in a bone or a missing piece of the bone material which starts on the outer surface of a bone and varies in depth, shape, and size and often contains uneven surfaces, the apparatus comprising:
    an elongated housing having a double chamber comprised of (1) a hollow outer chamber and (2) a hollow inner chamber positioned inside and surrounded by said hollow outer chamber,
    wherein both the inner chamber and the outer chamber have a proximal end and a distal end, wherein each of the inner and outer chambers has an opening on its proximal end, an opening on its distal end, and the opening on the proximal end is connected there-through to the opening on the distal end,
    wherein the outer chamber includes multiple ports that allow entry and exit of a first medium, wherein the first medium delivered into the outer chamber remains isolated from the inner chamber; and wherein the inner chamber allows entry of a second medium through its proximal end; and
    an inflatable balloon coupled to the distal end of the outer chamber of the elongated housing such that the only ingress and egress to the balloon is through the outer chamber, wherein the inflating of the inflatable balloon is performed through entry of the first medium from the outer chamber into the balloon, and wherein the first medium is contained within the boundaries of the inflatable balloon and the outer chamber thereby preventing leakage of the first medium outside the balloon and outer chamber to any of the surroundings of the apparatus,
    wherein the balloon in its inflated stage sits on the outside of the bone and surrounds the periphery of the void thereby creating a seal surrounding the void, wherein the seal allows deposition of the second medium through the inner chamber into the void without leakage of the second medium outside the sealed environment.

2. The apparatus of claim 1, wherein the first medium is liquid, gas, or other material to be used to inflate or deflate the balloon.

3. The apparatus of claim 1, further comprising an insertion device, wherein the insertion device can be inserted into the inner chamber from its proximal end.

4. The apparatus of claim 3, wherein the insertion device is a piston.

5. The apparatus of claim 1, wherein the second medium is gas, liquid, filler material or bone cement substance for filling bone defects.

6. An apparatus of claim 5, wherein said second medium comprises medication.

7. The apparatus of claim 1, wherein both the inner chamber and the outer chamber have a separate port that projecting outwardly from an outer surface of said housing.

8. The apparatus of claim 7, wherein the separate port of the outer chamber and the separate post of the inner chamber are located towards the proximal end of the apparatus.

9. The apparatus of claim 7, further comprising an insertion device, wherein the insertion device can be inserted into the inner chamber from its proximal end and pushed therethrough the inner chamber from its proximal end towards its distal end thereby pushing the second medium through the inner chamber to exit from its distal end and into the void.

10. The apparatus of claim 9, wherein the insertion of the insertion device into the inner chamber forms a seal from the outside environment preventing the entry or exit of air, liquid, or material from the inner chamber.

11. The apparatus of claim 7, wherein the inner chamber is used for storing or inserting filler material into a void and the outer chamber is used for inflating or deflating the inflatable balloon, and wherein the inner chamber is larger in volume than the outer chamber.

12. The apparatus of claim 11, wherein the port of the outer chamber is connected to an inflation source that allows insertion and extraction of a gas or liquid into the inflatable balloon for inflating and deflating the balloon to a desired size for creating a seal around the periphery of the void.

13. An apparatus of claim 1, further comprising a deposition tool located inside the inner chamber, wherein the deposition tool is capable of depositing solid matter, such as a fixation implant or device, inside the void.

14. An apparatus for use in a surgical environment for filling bone defect, wherein the bone defect is a void, the apparatus comprising:

an elongated tubular housing having a plurality of chambers, which includes an inner chamber having an inside wall and an outside wall, and an outer chamber surrounding said inner chamber, wherein each chamber is isolated from the other chamber, the inner chamber has an opening providing an entrance at the proximal end and an outlet at the distal end, wherein the inner chamber is used for housing material, a piston disposed in said inner chamber and movable relative to the chamber between the proximal end and the distal end of said inner chamber, wherein one end of the piston that is disposed in the said chamber includes a sealing engagement member that abuts the inner wall of the inner chamber thereby creating a seal between the inner wall of the inner chamber and the piston, and a plurality of inflatable balloons coupled to the elongated tubular housing, wherein one of the inflatable balloons is located at the distal end of the elongated tubular housing and is used for creating a seal between the void, its surrounding environment, and the apparatus thereby allowing deposition of material located in the inner chamber.

15. An apparatus of claim 14, wherein at least one of the plurality of inflatable balloons is attached on the outside of the elongated housing towards its proximal end thereby covering the entire outer periphery of the elongated housing and used for preventing any tissue from entering a surgical space.

16. An apparatus of claim 14, wherein the inflatable balloon at the distal end surrounds the outer periphery of the apparatus and is connected to at least one chamber, wherein the chamber includes a port that allows flow of air or gas from outside of apparatus to enter through the port and inflate the inflatable balloon, wherein the inflatable balloon in its inflated stage allows deposition of material into the void and thereafter containment of the material within the void while a pressurization technique is applied to push the material into the interstices of the bone for creating a strong bond due to interdigitation of the material with the bone.

* * * * *